United States Patent [19]

Sabel

[11] 3,949,757
[45] Apr. 13, 1976

[54] CATHETER FOR ATRIO-VENTRICULAR PACEMAKER

[76] Inventor: George H. Sabel, 336 Westwood Ave., Westwood, N.J. 07675

[22] Filed: May 13, 1974

[21] Appl. No.: 469,067

[52] U.S. Cl. .............................. 128/404; 128/419 P
[51] Int. Cl.² .......................................... A61N 1/04
[58] Field of Search ................. 128/404, 418, 419 P

[56] References Cited
UNITED STATES PATENTS

| | | | |
|---|---|---|---|
| 3,087,486 | 4/1963 | Kilpatrick | 128/418 |
| 3,729,008 | 4/1973 | Berkovits | 128/418 |
| 3,825,015 | 7/1974 | Berkovits | 128/404 |
| 3,865,118 | 2/1975 | Bures | 128/404 |

FOREIGN PATENTS OR APPLICATIONS 246,004   6/1969   U.S.S.R. ........................ 128/419 P

*Primary Examiner*—William E. Kamm
*Attorney, Agent, or Firm*—Bain, Gilfillan & Rhodes

[57] ABSTRACT

A catheter assembly for establishing independent electrical connection between a signal generating means and the surfaces of the atrium and ventricle of a heart is disclosed to include an atrial catheter conductor and a ventricular catheter conductor. The conductors are jointly mounted for concurrent introduction into the vicinity of the heart. The atrial catheter is slidably received within an insulating means the terminal end of which is displaced from the distal tip of the ventricular catheter conductor so that the ventricular catheter conductor first may be positioned in electrical contact with the ventricular surface whereafter the atrial catheter conductor may be slidably extended from the insulating means to a position in electrical contact with the surface of the atrium.

1 Claim, 7 Drawing Figures

U.S. Patent    April 13, 1976    3,949,757
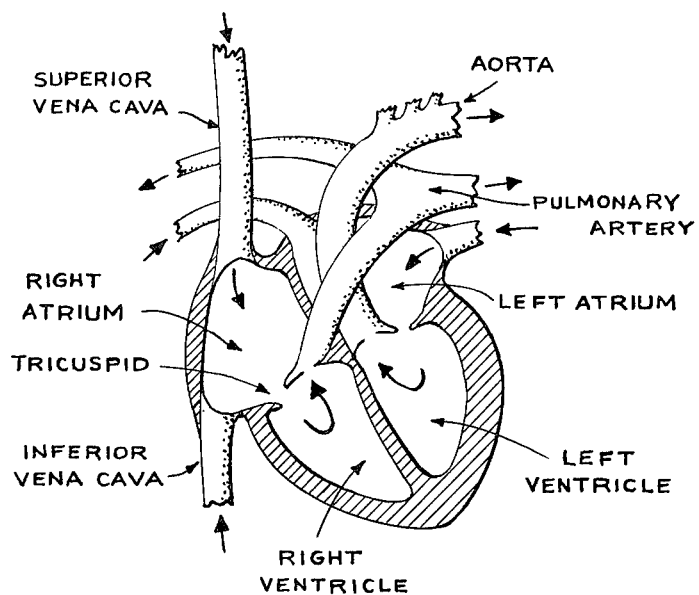
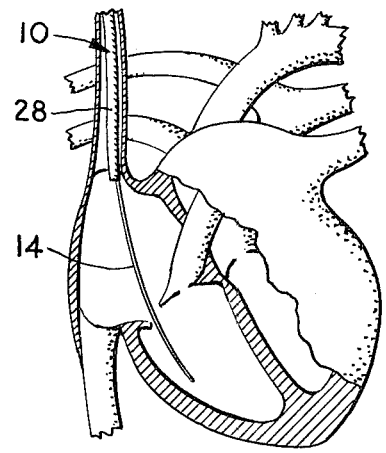
FIG. 5
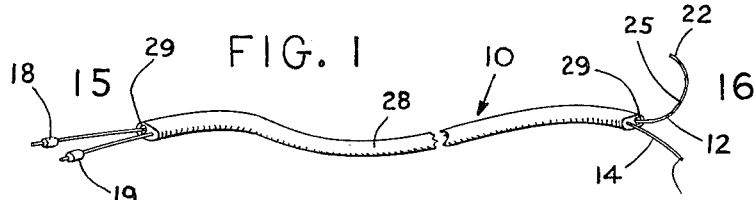
FIG. 1
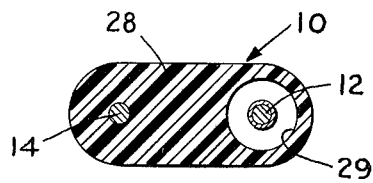
FIG. 3
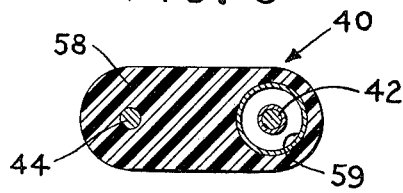
FIG. 4
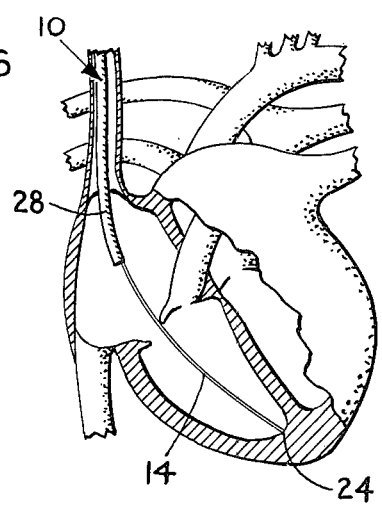
FIG. 6
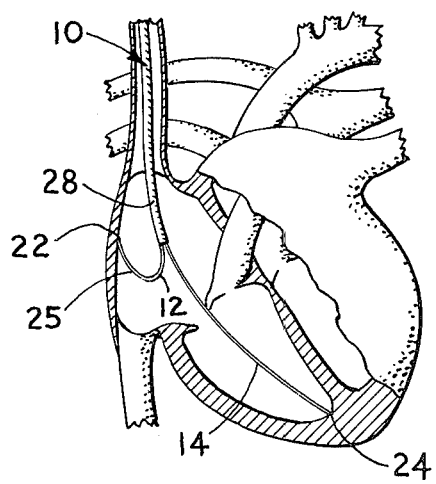
FIG. 7

CATHETER FOR ATRIO-VENTRICULAR PACEMAKER

BACKGROUND

This invention relates generally to the field of catheters. More specifically, this invention relates to catheters for establishing independent electrical contact between an electrical signal generating means and the surfaces of the atrium and ventricle of a heart.

As is recognized clearly by those skilled in these arts the rhythm of the beat of the heart is controlled naturally by a small mass of specialized muscle tissue in the heart known as the sino-atrial node (SA node).

In some cases of heart disorder or heart disease, however, the heart becomes unable to regulate its own pumping frequency. It is known that in such cases the frequency of heart pumping or heart beat may be artificially regulated by electrical stimulation. Thus electrical signal generating devices (pacemakers) are known which introduce an electrical pulse, for example a fine milliampere pulse, to the ventricle of the heart through a catheter.

Most known pacemakers in use are designed for ventricular pacing, i.e., to generate a signal which is carried through an implanted catheter conductor to the right ventricle of the heart thus providing direct stimulation only to the ventricle. This of course is not totally consistent with the normal pacing of the heart wherein the SA node operates to cause the atria to contract first, forcing blood into the ventricles which are then stimulated to contract and pump blood into the circulatory systems of the body.

In ventricular pacing, where the benefit of cooperative action between atrium and ventricle is absent, the inefficiency resulting from incomplete atrial filling of the ventricle may cause reduction in cardiac output by as much as twenty percent. Although such a reduction is acceptable in some patients it may well be critical in others and in such cases may result in heart failure or severe hypotension.

These problems attendant to ventricular pacing have not gone unrecognized. Various manufacturers have developed dual signal generating pacemakers which are designed either to pace the atria and ventricles in succession or to sense the patient's atrial contraction so as to pace the ventricle in response thereto a fraction of a second later.

The operation of such dual signal generating pacemakers requires an independent electrical connection between the pacemaker and the surfaces of the atrium and ventricle which are being stimulated or sensed. The presently practiced mode of establishing such electrical connection is to pass independent catheters through separate veins and into the atrium and ventricle to be served. Known atrial catheters have been unsatisfactory because of the inability to maintain a satisfactory electrical connection between the catheter conductor and the surface of the atrium which, unlike the surface of the ventricle, is smooth and unreceptive to the permanent lodging of a conductor tip.

SUMMARY OF THE INVENTION

It is an object of the present invention, therefore, to provide a catheter for multiple signal generating pacemakers wherein the ability of the atrial catheter conductor to maintain electrical contact with the surface of the atrium is improved.

An additional object of the present invention is to provide a catheter for multiple signal generating pacemakers wherein the atrial catheter conductor and the ventricular catheter conductor may be introduced to the heart through a single vein.

A further object of the present invention is to provide a catheter for multiple signal generating pacemakers wherein the atrial catheter conductor is provided with support for improving the electrical contact between the conductor and the surface of the atrium.

Still another object of the present invention is to provide a catheter for multiple signal generating pacemakers wherein both atrial and ventricular catheters may be introduced to the heart together, the ventricular catheter may be positioned within the ventricle and in surface contact with the ventricle wall and thereafter the atrial conductor may be positioned to be in electrical contact with the surface of the atrium.

These objects and others not enumerated are achieved by the present invention in catheter assemblies, one embodiment of which may include a first conductor for establishing electrical connection between a signal generating means and the surface of a ventricle, a second conductor for establishing electrical connection between the signal generating means and the surface of the atrium, a first insulating covering on the first conductor extending from one end of the conductor to a point adjacent its distal or ventricle contacting end, a second insulating covering disposed upon the second conductor from a point adjacent one end thereof to a point adjacent the distal or atrial contacting end, said second conductor being slidable with respect to said first conductor for effecting electrical contact with the wall of the atrium.

BRIEF DESCRIPTION OF THE DRAWINGS

A more complete understanding of the invention may be had from the following detailed description thereof, particularly when read in the light of the accompanying drawings, wherein:

FIG. 1 is a schematic cross-sectional view of a human heart with respect to which a catheter assembly according to the present invention may be used;

FIG. 2 is a schematic view of a catheter assembly according to the invention;

FIG. 3 is a partially cut-away cross-sectional view of one embodiment of catheter assembly according to the invention;

FIG. 4 is a partially cut-away cross-sectional view of a second embodiment of catheter assembly according to the invention;

FIG. 5 is a view similar to FIG. 1 but showing only the right side of the heart with related arteries and veins and showing an initial step of introducing a catheter assembly according to the invention;

FIG. 6 is a view similar to FIG. 5 but showing the catheter assembly of the invention with the ventricular conductor in place and with the atrial conductor withdrawn; and FIG. 7 is a view similar to FIGS. 5 and 6 but showing the catheter assembly of the invention with both the atrial and ventricular catheter conductors in operating engagement with the surfaces of the atrium and ventricle respectively.

DETAILED DESCRIPTION

The present invention relates to catheters for use with multiple signal generating pacemakers. Such catheters operate to conduct heart stimulating electrical impulses from pacemakers to the surfaces of the chambers of the heart.

Referring therefore to FIG. 1, there is shown schematically and for purposes of reference a human heart having right and left ventricles and right and left atria. Blood returning to the heart from the body through the superior and inferior vena cava passes into the right atrium wherefrom it is pumped through the tricuspid valve and into the right ventricle. Contraction of the right ventricle causes the tricuspid to close in response to the generated pressure and the blood to flow outwardly through the pulmonary arteries. After having passed through the lungs, oxygenated blood returns to the left atrium where it is boosted into the left ventricle and thereafter pumped into the body through the aorta.

Under known procedures for introducing a catheter intravenously, the catheter may be introduced into any of the jugular, subclavian or antecubital veins and advanced through the superior vena cava into the right atrium. Further advancement causes the catheter to pass through the tricuspid valve and into the right ventricle. Ordinarily the catheter electrode is wedged into the inferior wall of the right ventricle pointing toward the apex. The external portion of the catheter is then secured with a ligature at the point of exit from the vein. As is discussed below in detail, the same general procedure may be followed for introducing an atrio-ventricular catheter according to the present invention.

Considering, therefore, a catheter assembly according to the present invention, such as assembly is shown schematically in FIG. 2 and designated generally by the reference numeral 10. Catheter assembly 10 comprises an atrial catheter 12 and a ventricular catheter 14 disposed in longitudinally extending side-by-side relationship.

Catheter assembly 10 has a proximal end 15, which is the end at which the catheter assembly is connected to a pulse generator or pacing device, and a distal end 16 which is the end designed for introduction into the heart. Atrial catheter 12 at its proximal end is provided with a connector 18 which, in the embodiment shown is a male-end jack type connector. Similarly, the proximal end of ventricular catheter 14 is provided with a connector 19 which in the embodiment shown also is a male-end jack type connector. It will be recognized by those skilled in these arts that connectors other than jack type connectors may be utilized to connect catheter conductors to pacing devices and their use in substitution for those disclosed is contemplated at the discretion of the user.

The distal ends of atrial and ventricular catheters 12, 14 are provided with electrodes 22, 24 respectively. Such electrodes may be manufactured from any suitable materials, e.g. platinum or gold, as is recognized by those skilled in these arts. The conductive wires between the respective connectors 18, 19 and their related electrodes 22, 24 may be of the accepted conductive materials suitable for use, e.g., stainless steel.

With the exception of the connector 18, 19 and the electrodes 22, 24, the remaining portions of atrial and ventricular catheters 12, 14 and in particular the conductive wires, are coated with a suitable insulating material which may be selected from any of the many generally known and available in these arts, e.g. a biologically inert plastic such as SILASTIC.

For reasons set out in detail below, atrial catheter 12 is provided with a pre-set curvilinear portion 25 adjacent its distal end. The curvilinearity may be provided in manners known in the arts (see, e.g., U.S. Pat. No. 3,729,008 to Berkovits). The curvilinearity may be provided commencing at a point adjacent but behind atrial electrode 22 for a distance ranging between 6 mm and 10 mm displaced from electrode 22.

In the embodiment of catheter assembly shown in FIG. 3, both atrial catheter 12 and ventricular catheter 14 are disposed within a sheath 28. Sheath 28, which may be of any suitable plastic non-rejective material rigidly contains ventricular catheter 14. Thus in manufacture, the assembly 10 may be formed by extruding the material of sheath 28 directly on ventricular catheter 14 (or directly on the conductor of catheter 14) while at the same time extruding the sheath material such as to define a longitudinally extending passage 29 within which atrial catheter 12 may be received slidably. More specifically, sheath 28 is intended to be in rigid contact with ventricular catheter 14 while providing a passage 29 within which atrial catheter 12 may be longitudinally displaced. For reasons discussed below in detail, the amount of possible displacement of atrial catheter 12 within passage 29 of sheath 28 must be at least sufficient to permit withdrawal of the distal end of catheter 12 into passage 29 while also permitting extension of the distal end of atrial catheter 12 by a distance sufficient to completely uncover curvilinear portion 25.

Considering now what appears to be the more desirable procedure for introducing and placing a catheter assembly 10 in accordance with the invention, and with particular reference to FIGS. 5, 6 and 7, a catheter assembly 10 with atrial catheter withdrawn into passage 29 is passed into the right atrium through the superior vena cava after having been introduced through any of the jugular, subclavian or antecubital veins (FIG. 5).

With atrial catheter 12 remaining in the withdrawn position catheter assembly 10 continues to be advanced such that ventricular catheter 14 passes through the tricuspid valve and into the right ventricle until electrode 24 wedges against the ventricular wall (FIG. 6).

With the ventricular catheter so positioned, atrial catheter 12 is displaced within passage 29 of sheath 28 such that the electrode 22 is exposed within the right atrium and thereafter progressively the curvilinear portion 25. As the curvilinear portion continues to be uncovered from passage 29 electrode 22 will be displaced toward the atrium wall until surface-to-surface contact is made. Thereafter the atrial catheter 12 is advanced slightly additionally such as to establish a resilient stress condition in the atrial catheter between the electrode 22 contacting the atrium wall and the sheath 28 which cooperates with ventricular catheter 14 to define a reaction support. As now will be evident to those skilled in these arts, the atrial electrode 22 so positioned will be maintained in positive surface-to-surface contact with the atrium wall by the cooperation of curvilinear portion 25 with sheath 28 and ventricular catheter 14.

A second embodiment of catheter assembly is shown in FIG. 4 and designated generally by the reference numeral 40. Assembly 40 comprises an atrial catheter 42, a ventricular catheter 44 and a sheath 58. In this embodiment, however, sheath 58 comprises a container in which is received the ventricular catheter and a tube 59 which defines the passage within which atrial catheter 42 may be slidably received. The advantage of structuring a catheter assembly in the manner shown in FIG. 4 is that sheath 58 may be formed by extruding sheathing material directly upon ventricular catheter 14 and tube 59 while passing both through a die concurrently. This, of course, is a much less complex extrusion than that which would be required to form the assembly of FIG. 3; however, each is within the skill of those having ordinary skill in the extrusion arts.

Although only two embodiments of the invention have been disclosed it will be recognized that other structures are possible which would fall within the scope of this teaching. For example, it would appear possible to utilize the sheathing material as insulation for the ventricular conductor. Such modifications and others not enumerated are submitted to be within the spirit and scope of the present invention.

I claim:

1. A catheter assembly for establishing independent electrical connection between a signal generating means and the surfaces of the atrium and ventricle of a heart, comprising:

a first catheter for establishing electrical connection between said signal generating means and said surface of said ventricle, said first catheter including a conductor with a connector end for electrical connection with said signal generating means and a distal tip for establishing electrically conductive contact with said surface of said ventricle;

a first insulating covering rigidly encapsulating said first conductor from a point adjacent said connector end to a point adjacent said distal tip, said first insulating covering having a longitudinally extending passage formed therein, said passage extending from a point adjacent to the conductor end of said first catheter to a point displaced from said distal tip of the conductor of said first catheter;

a second catheter slidably disposed within said passage, said second catheter for establishing electrical connection between said signal generating means and said surface of said atrium, said second catheter including a conductor having a connector end for electrical connection with said signal generating means and a distal tip for establishing electrically conductive contact with said surface of said atrium, said second catheter being flexible and including a resiliently curvilinear portion adjacent to said distal tip, said resiliently curvilinear portion being flexible between rectilinear and curvilinear configuration in response to sliding said second catheter longitudinally with respect to said first catheter within said longitudinally extending passage; and a second insulating covering disposed upon said conductor of said second catheter from a point adjacent to said connector and to a point adjacent to said distal tip connector.

* * * * *